United States Patent [19]
Shibuya et al.

[11] Patent Number: 6,153,227
[45] Date of Patent: Nov. 28, 2000

[54] PROPOLIS EXTRACT

[75] Inventors: Takashi Shibuya, Okayama; Kazuyuki Oku, Hiroshima; Hajime Aga; Shigeharu Fukuda, both of Okayama, all of Japan

[73] Assignee: Kabushiki Kaisha Hayashibara Seibutsu Kagaku Kenkyujo, Okayama, Japan

[21] Appl. No.: 09/363,851

[22] Filed: Jul. 30, 1999

[30] Foreign Application Priority Data

Jul. 31, 1998 [JP] Japan .................................. 10-216371

[51] Int. Cl.⁷ .......................... A61K 35/64; A61K 35/78; B01D 15/00
[52] U.S. Cl. ...................... 424/539; 424/537; 424/195.1; 210/660; 422/5
[58] Field of Search ................................ 424/195.1, 539, 424/537; 210/660; 422/5

[56] References Cited

U.S. PATENT DOCUMENTS 5,743,940  4/1998  Sugo et al. .

FOREIGN PATENT DOCUMENTS

| 0529962 | 3/1993 | European Pat. Off. . |
|---|---|---|
| 3210272 | 9/1983 | Germany . |
| 1165595 | 6/1989 | Japan . |
| 5316968 | 12/1993 | Japan . |
| 9141002 | 3/1997 | Japan . |

OTHER PUBLICATIONS

English abstract of Japanese Patent No. 55,144,879 A2, Nov. 1980.
Wada et al., "Objective Evaluation of Varieties of Coffee by Coupling of Analytical Data and Multivariate Analyses", *Agric. Biol., Chem.,* vol. 57, No. 7, pp. 1753–1760, (1987).
Matsuda, "Food and Food Ingredient Journal of Japan", vol. 160. pp. 64–73, (1994).
Japanese Society of Chemotherapy, "Chemotherapy", vol. 27, pp. 559–560, (1979).
Japanese Society of Chemotherapy, "Chemotherapy", vo. 29, pp. 76–79, (1981).
Patent Abstracts of Japan, JP–01165595, Jun. 29, 1989.
Patent Abstracts of Japan, JP–63145207, Jun. 17, 1988.
Patent Abstracts of Japan, JP–05059391, Mar. 9, 1993.
Patent Abstracts of Japan, JP–07255391, Oct. 9, 1995.

*Primary Examiner*—Leon B. Lankford, Jr.
*Assistant Examiner*—Susan D. Coe
*Attorney, Agent, or Firm*—Browdy and Neimark

[57] ABSTRACT

Disclosed are a propolis extract where the peculiar odor of propolis is reduced by decreasing the odorizing ingredients, a process to produce the propolis extract which comprises soaking propolis in a hydrophilic organic solvent to effect extraction and treating the liquid layer in the resultant extract with an anion-exchange resin, and a biologically active composition comprising the propolis extract.

4 Claims, 1 Drawing Sheet

6,153,227

PROPOLIS EXTRACT

BACKGROUND OF THE INVENTION

1. Field of the Invention

This invention relates to a novel propolis extract, in particular, to a propolis extract where the peculiar odor of propolis is reduced.

2. Description of the Prior Art

Propolis is known as a sticky substance which is used to build the beehives: It is said that there are present in intact propolis a variety of trace ingredients in form of a homogenous mixture with resins, beeswax, essential oils and pollens as predominant ingredients. Propolis has been used from ancient times as medicine for folk remedy in different areas in the world because of its potential antimicrobial and lenitive activities. As described in Shinobu Matsuda, "Foods and Food Ingredients Journal of Japan", No.160, pp.64–73 (1994), recently, other ingredients such as flavonoids and phenol carboxylic acids have been isolated and identified one after another. With the advances in identification and clarification of particular ingredients and their biological activities, the usefulness of propolis as life improving means has been highlighted, thus a variety of health-care and supplemental health-care products have appeared in the market.

By the way, intact propolis is not suitable for use in food products because it usually contains large amounts of contaminants and hardly dissolves in water. In commercialized health-care and supplemental health-care products, propolis is added in the form of extracts which are obtained through the step of soaking crushed propolis mass in ethanol, glycerol and/or water. Propolis has a peculiar odor, which is one of the drawbacks to be overcome but however still not overcome in currently available propolis extracts, thus restricting their use to a few types of food products. Although Japanese Patent Kokai Nos. 165,595/89 and 316,968/93 propose several approaches to improve the appearance and smell of propolis extracts using activated charcoals, synthetic porous adsorbents and cation-exchange resins, each of the approaches has been proved unsuccessful in reducing the peculiar odor of propolis.

SUMMARY OF THE INVENTION

In view of the foregoing, the first object of this invention is to provide a propolis extract where the peculiar odor of propolis is reduced.

The second object of this invention is to provide a process to produce such a propolis extract.

The third object of this invention is to provide several uses of such a propolis extract.

The present inventors investigated the odorizing ingredients in propolis using gas chromatography and sensory test in combination, resulting in the finding that on gas chromatography using p-ethyl phenol as internal standard, one major odorizing ingredient gives a relative retention time against p-ethyl phenol of 0.7–0.8, and another major odorizing ingredient, a relative retention time against p-ethyl phenol of 1.2–1.3. The present inventors further investigated various procedures which may remove such ingredients, eventually finding that the ingredients can be successfully removed by soaking propolis in hydrophilic organic solvents to effect extraction, and treating the liquid layer in the resultant extract with anion-exchange resins: Thus the peculiar odor of propolis can be reduced without attenuating the biological activities inherent to propolis. Further, the present inventors confirmed that the propolis extract thus obtained is favorably feasible in various uses which have been never realized with conventional propolis extracts because of the peculiar odor of propolis, in addition to the same uses as in conventional propolis extracts, thus completing this invention.

More particularly, to attain the first object, this invention provides a propolis extract where the content of an odorizing ingredient with a relative retention time against p-ethyl phenol of 0.7–0.8 as determined on gas chromatography using p-ethyl phenol as internal standard, and/or another odorizing ingredient with a relative retention time of 1.2–1.3 determined similarly as above is or are reduced.

To attain the second object, this invention provides a process to produce such a propolis extract, comprising soaking propolis in a hydrophilic organic solvent to effect extraction, and treating the liquid layer in the resultant extract with an anion-exchange resin.

To attain the third object, this invention provides a biologically active composition which contains such a propolis extract.

BRIEF EXPLANATION OF THE ACCOMPANYING DRAWINGS

Figure 1:
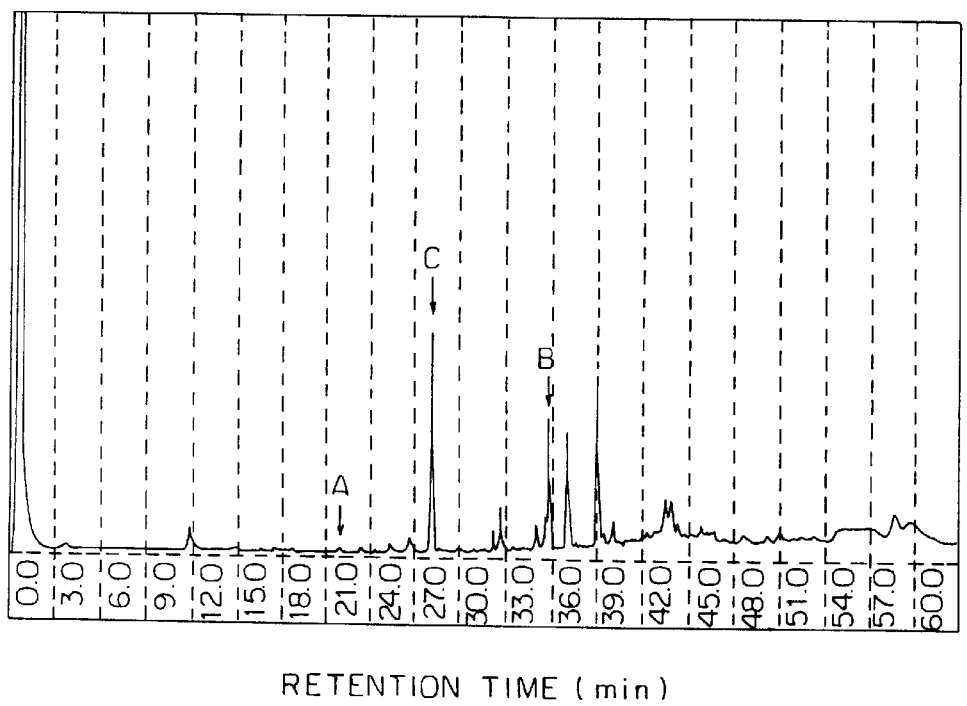
FIG. 1 is the gas chromatogram of a propolis extract which has been treated with an anion-exchange resin.
Figure 2:
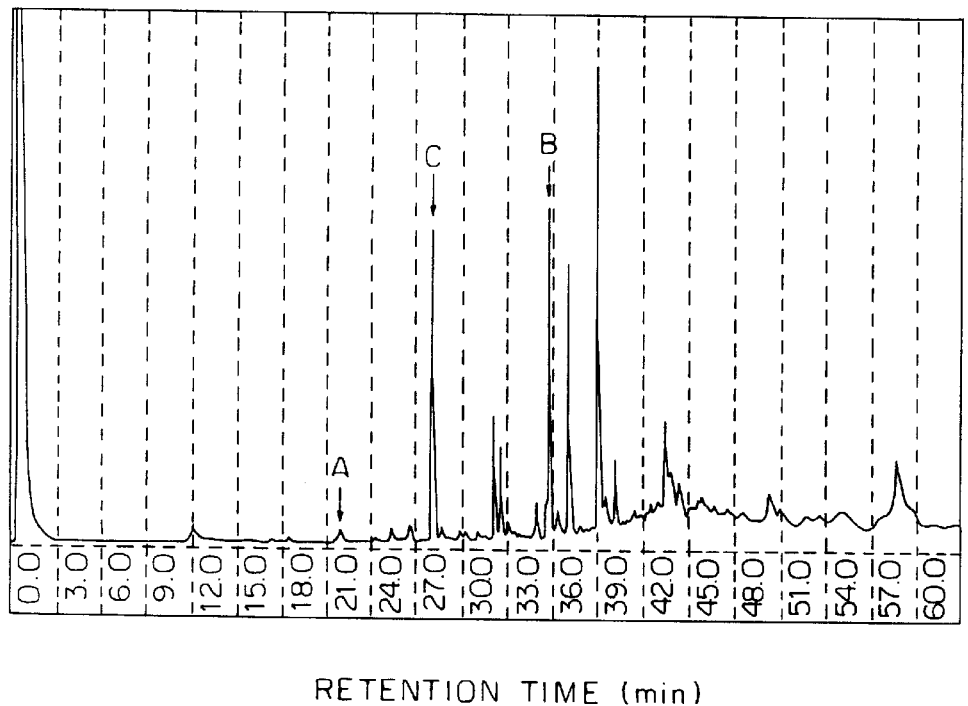
FIG. 2 is the gas chromatogram of another propolis extract which has not been treated with anion-exchange resin.

In FIGS. 1 and 2, the symbol "A" indicates the peak of the odorizing ingredient A; "B", the odorizing ingredient B; and "C", the internal standard p-ethyl phenol.

DETAILED DESCRIPTION OF THE INVENTION

This invention is based on the identification of odorizing ingredients in propolis and discovery of means which enable successful removal of the ingredients. As described heretofore, major odorizing ingredients in propolis give a relative retention time against p-ethyl phenol of either 0.7–0.8 or 1.2–1.3 on gas chromatography using p-ethyl phenol as internal standard. Conventional propolis extracts contain the former odorizing ingredient in an amount not less than 4 mg/g of solid, and the latter odorizing ingredient in an amount not less than 60 mg/g of solid, dependently on the source of propolis as starting material and way of extraction. Further, the results of sensory test confirmed that the peculiar odor of propolis is reduced when the content of the former and/or latter odorizing ingredient(s) is or are reduced, as well as that the peculiar odor become substantially not to be perceived when the former and latter odorizing ingredients are less than 2.5 mg/g-solid and 40 mg/g-solid respectively. Thus, the wording "propolis extract of this invention" as referred to in this invention includes propolis extracts in general regardless of their nature and source of propolis as starting material as well as of way of preparation, as long as their content of an odorizing ingredient having a relative retention time against p-ethyl phenol of 0.7–0.8 as determined on gas chromatography using p-ethyl phenol as internal standard, and/or another odorizing ingredient with a relative retention time against p-ethyl phenol of 1.2–1.3 determined similarly as above is or are reduced.

Such a propolis extract can be prepared in desired amounts by the process according to this invention, comprising the step of extraction using hydrophilic organic solvents, and treatment with anion-exchange resins. In the process according to this invention, propolis is first soaked in a hydrophilic organic solvent to effect extraction, then the liquid layer in the resultant extract is collected and treated with an anion-exchange resin to remove odorizing ingredients. As to the source of propolis as starting material, one can use those from Japan, South America, North America, Australia, China and Europe: Propolis in massive form may be crushed and/or pulverized prior to extraction in order to improve extraction efficiency. The wording "hydrophilic organic solvent" as referred to in this invention includes any organic solvents, as long as they dissolve in water: Preferred hydrophilic solvents are, for example, lower alcohols such as methanol, ethanol, n-propanol and isopropanol which are usually used in mixture with water.

As to extraction conditions, propolis is soaked in equivolume, preferably, 5-fold volume of either hydrophilic organic solvent or a mixture of hydrophilic solvent and water, and extracted at a temperature exceeding ambient temperature, usually, 40° C. or higher, preferably, 50°–80° C. for 0.5 hours or longer, preferably, 1 hour or longer while stirring. Usually, extraction is repeatedly conducted: For example, in the case of using a mixture of hydrophilic organic solvent and water, the ratio of hydrophilic solvent is first set to a lower level, then elevated stepwise in every repeated extraction. More particularly, propolis is soaked in such a mixture with a content of hydrophilic organic solvent of 30% (v/v) or less, then the solid layer is collected and soaked again in a mixture with a content for hydrophilic organic solvent exceeding 30% (v/v) to effect further extraction. In this case, one can favorably conduct extraction when the counter current method is employed in a continuous or semi-continuous manner. The propolis which has been subjected to such an extraction consists of a solid layer, which is rich in contaminants, and a liquid layer which is rich in biologically active ingredients. The liquid layer is collected by, for example, filtration, decantation and/or centrifugation, adjusted to a desired concentration, if necessary, and then transferred to the treatment step using anion-exchange resin.

The wording "anion-exchange resin" as referred to in this invention means strongly, intermediately and weakly basic anion-exchangers in general, which comprise a polymer base of three-dimensionally polymerized hydrocarbons in powder, granule, bead or hollow fiber form, and primary amino groups, secondary amino groups, tertiary amino groups and/or quaternary ammonium groups as ion exchange groups bound on the polymer base. Commercially available anion-exchange resins are, for example, "DIAION WA-10", "DIAION WA-11", "DIAION WA-20", "DIAION WA-21" and "DIAION WA-30" (products of Mitsubishi Chemical Corp., Tokyo, Japan), "AMBERLITE IRA411S", "AMBERLITE RA458" and "DUOLITE A-30B" (products of Rohm and Haas Co., Philadelphia, Pa., U.S.A.), and "A21" and "A26" (products of Japan Organo Co., Ltd., Tokyo, Japan), which may be used in combination with cation-exchange resins and/or synthetic porous adsorbent, if necessary. One can easily obtain high-quality propolis extracts when anion-exchange resins are used in combination with cation-exchange resins.

The liquid layer can be treated batchwise or in continuous manner: When the liquid layer to be treated is in large amount, it is much more favorable to employ a continuous operation where anion-exchange resin is packed in column inside a cylindrical tube of glass, ceramic or stainless steal. In each case, anion-exchange resin is used at 1% or more, preferably, 5% or more in wet weight against the amount of solutes in liquid layer to be treated, and the treating conditions are adequately modulated so that the liquid layer is kept in contact with anion-exchange resin over a time period of 0.1 hour or longer, preferably, 0.5 hours or longer. For example, in the case of using anion-exchange resin packed in column, a mixture of hydrophilic organic solvent and water is applied through the column for its equilibration, and the liquid layer is loaded through one end of the column, followed by applying a fresh preparation of the same mixture as described above at SV5 or less, preferably, SV3 or less. The eluate from the column can be fractionated, and the fractions with biologically active ingredients are collected, pooled and concentrated followed by dehydrating into solution, syrup or solid, if necessary. In the propolis extract obtained according to this invention, usually, the peculiar odor of propolis is substantially eliminated and this may render the extract odorless.

The propolis extract of this invention bears the biological activities inherent to propolis, for example, antimicrobial activity, antiviral activity, antitumor activity, anti-inflammatory activity, anti-hyperlipemic activity, local anesthesia activity, immune-regulatory activity, apoptosis-regulatory activity, anti-oxidative activity, ultra violet ray-absorbing activity, preservative activity and vitamin P-supplying activity. The propolis extract of this invention is favorably usable alone or in combination with other biologically active compositions in the fields of foods, cosmetics (including toiletries) and pharmaceuticals, as well as in other fields where the biological activities of propolis are needed. Thus, the wording "biologically active composition" as referred to in this invention incudes any compositions regardless of their form, as long as they are formulated with the propolis extract of this invention and feasible in the fields as described above where the biological activities of propolis are needed and used. Such a composition is usually provided in forms which are feasible in the above described field without further processing, as well as in the form of starting materials and ingredients which are used in the preparation of final products and, further, in the form of intermediates which are added in any stages of preparing final products.

The use of the propolis extract of this invention in particular fields will be further explained in detail: In the field of foods, the present propolis extract can be favorably used alone as supplemented heath-care product or together with other one or more materials and/or ingredients which are usually used in food products, for example, water, alcohols, starches, proteins, dietary fibers, saccharides, lipids, vitamins, minerals, flavorings, colorings, sweeteners, seasonings, spices, emulsifiers, antiseptics, preservatives, fungicides, germicides and antioxidants, to facilitate the intake of the propolis extract of this invention. The biologically active composition according to this invention is prepared into solution, emulsion, syrup, cream, paste, jelly, powder, granule and other desired solid forms to meet to particular final uses. The biologically active composition directed to use in the field of foods usually contains the present propolis extract in an amount of 0.001% (w/w) or more, preferably, 0.005% (w/w) or more on a dry solid basis (d.s.b.).

Particular forms in foods are, for example, seasonings such as a soy sauce, powdered soy sauce, "miso", "funmatsu-miso" (a powdered miso), "moromi" (a non-refined sake), "hishio" (a non-refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, "chuka-no-moto" (a seasoning for Chinese dish), instant stew mix, instant soup mix, "dashi-no-moto" (an instant stock mix), mixed seasoning, "mirin" (a sweet sake), "shin-mirin" (a synthetic mirin), table sugar, and coffee sugar; "wagashi" (Japanese cakes) such as a "senbei" (a rice cracker), "arare" (a baked rice cake), "okoshi" (a millet-and-rice cake), "karinto" (fried dough cake), "gyuhi" (starch paste), "mochi" (a rice cake), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella, and "amedama" (a Japanese toffee); confectioneries such as a biscuit, cracker, cookie, pie, pudding, cream puff, waffle, sponge cake, doughnut, chocolate, chewing gum, caramel, candy, and gummy jelly; frozen desserts such as an ice cream, ice candy, and sherbet; syrups such as a "korimitsu" (a sugar syrup for shaved ice); spreads and pastes such as a butter cream and custard cream; processed fruits and vegetables such as a jam, marmalade, "syrup-zuke" (a fruit pickle with a syrup), and "toka" (a conserve); processed cereal foods such as a bun, noodle, cocked rice, and artificial meat; oil and fat foods such as a salad oil and margarine; pickles or pickled products such as a "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles or pickled products such as a "takuan-zuke-no-moto" (a premix for pickled radish), and "hakusai-zuke-no-moto" (a premix for fresh white rape pickles); meat products such as a ham and sausage; fish products such as a fish ham, fish sausage, "kamaboko" (a steamed fish paste), "chikuwa" (a kind of fish paste), and "hanpen" (a Japanese deep-fat fried fish paste); "chinmi" (relishes) such as an "uni-no-shiokara" (salted guts of sea urchin), "ika-no-shiokara" (salted guts of squid), "su-konbu" (a processed tangle), "saki-surume" (dried squid strips), and "fugu-no-mirin-boshi" (a dried mirin-seasoned swellfish); boiled foods such as those cooked with agricultural products, livestocks, and fisheries; daily dishes such as a boiled food, grilled food, fry, fried food, steamed food, and dishes dressed with sauce; frozen foods such as those of shrimp for frying, croquette, shao-mai, "gyoza" (fried or steamed dumpling stuffed with minced pork), "harumaki" (a kind of Chinese dish), hamburger steak, meat ball, fish hamburger, or fish ball; retort foods such as those of a hamburger, meat ball, rice boiled together with red beans, rice boiled with beef or chicken, gruel of unpolished rice, curry, meat sauce, demiglace sauce, potage soup, consomme soup, stew, Japanese hotchpotch, "happosai" (a kind of Chinese vegetable dish with meats and fish), boiled bean, grilled chicken, pot-steamed hotchpotch, boiled chestnut, and water-boiled vegetable; egg and milk products such as a "kinshi-tamago" (a stripped egg roll), milk beverage, butter, and cheese; canned and bottled products such as those with meats, fish meats, fruits, or vegetables; alcohols such as a synthetic sake, sake, wine, and liquor; soft drinks such as a coffee, cocoa, juice, green tea, black tea, Oolong tea, mineral beverage, carbonated beverage, sour milk beverage, and beverage containing lactic acid bacteria; and instant food products such as an instant pudding mix, instant hot cake mix, instant juice, "sokuseki-shiruco" (an instant mix of adzuki-bean soup with rice cake), and instant soup mix. In addition to foods for humans, the present propolis extract can be also used in feeds and pet foods for animals such as domestic animals, poultry, honey bees, silk worms, and fishes.

In the field of cosmetics, including toiletries, the present propolis extract can be, while used alone, favorably used together with one or more commonly feasible ingredients for cosmetics to facilitate the application of the extract. Examples of the feasible ingredients are oily bases, aqueous bases, -flavorings, colorings, dyes, refrigerants, humectants, emollients, emulsifiers, gelatinizers, viscosity enhancers, softening agents, solubilizers, surfactants, foam-stabilizers, stabilizers, clearances, adipositas agents, putrefactive agents, coating-forming agents, propellants, antisepses, preservatives, and antioxidants. The composition can be incorporated further together with one or more agents such as vitamins, amino acids, peptides, hormones, extracts, vasodilators, blood circulation-improving agents, cell-activators, germicides, anti-inflammatory drugs, urtication-preventing agents, astringents, skin-function-promoting agents, and keratolytics. The composition is prepared into solution, emulsion, cream, paste, powder, granule and other desired solid forms to conform to the particular final uses. The biologically active composition directed to use in the field of cosmetics usually contains the present propolis extract in an amount of 0.001% (w/w) or more, preferably, 0.005% (w/w) or more (d.s.b.).

Particular examples of the present biologically active composition in the form of cosmetics are those for hair such as hair restorers and hair growth-promoting agents, pomades, hair sticks, hair oils, hair creams, hair solids, hair liquids, hair set lotions, hair styling-gels, hair water-greases, hair mousses, hair aerosols, hair liquids for permanent wave, and hair dyes; those for washing such as shampoos for hair and body, hair rinses, hair-washing soaps, cosmetic soaps, and setting foams; those for skins such as cosmetic water, creams, milky lotions, lotions, packs, foundations, lip sticks, rouges, eye liners, mascara, eye shadows, eyebrow pencils, manicures, and powders; those for oral uses such as tooth powders, moisturized dentifrices, toothpastes, tooth washes, medical dentifrices, cachous, and gargles; and other cosmetics such as sunscreens, shaving cosmetics, bath cosmetics, perfumes, eau de colognes, underarm deodorants, baby powders, eye lotions, and bleaching creams. In the cosmetics for skins or hair, the present propolis extract more readily functions when co-incorporated with $\alpha$-glycosyl bioflavonoids such as $\alpha$-glucosyl rutin, $\alpha$-glucosyl hesperidin, and $\alpha$-glucosyl naringin in a final amount of about 0.001% (w/w) to about 10% (w/w), because the bioflavonoids promote the supplement of nutrients to skins and the metabolism of living bodies. The present propolis extract also more readily functions when co-incorporated with humectants such as moisture-retaining saccharides or sugar alcohols, for example, maltose, trehalose, and maltitol at an appropriate content, preferably, in a final amount of 1% (w/w) or lower, because the humectants keep the skins, scalps, and/or hair well moistened.

In the field of pharmaceuticals, the present propolis extract can be used in pharmaceutical compositions to treat and/or prevent the present extract-susceptive diseases such as infections, autoimmune diseases, malignant tumors, and hyperlipemias, which may emerge in the alimentary system, circulating system, urinary and genital organs, brain and nervous system, eye, ear, nose, throat, or skin.

In the field of pharmaceuticals, an effective amount of the present propolis extract can be used alone or, if necessary, together with one or more conventional agents for pharmaceuticals. Examples of the conventional agents are anesthetics, hypnotic sedatives, anti-anxieties, antiepileptics, antipyretic antiphlogistics, stimulants, wake amines, anti-parkinson drugs, agents for psychoneuroses, agents for central nervous system, skeletal muscle relaxants, agents for autonomic nervous system, antispastic agents, drugs for eye, drugs for nose and ear, anti-vertiginous drugs, cardiotonics, antiarrhythmic drugs, diuretics, pressure reduction drugs, vasoconstrictors, coronary vaso-dilators, peripheral vasodilating drugs, hyperlipemia drugs, breath stimulants, antitussive and expectorant drugs, bronchodilators, drugs for allergy, antidiarrheal drugs, drugs for intestinal disorders, peptic ulcer drugs, stomachic digestants, antacids, cholagogouses, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasitic skin diseases, skin-softening drugs, caustics, dental/oral drugs, vitamins, inorganic preparations, supplemental liquids, hemostatics, anticoagulation drugs, drugs for liver diseases, antidotes, habitual intoxication drugs, drugs for treatment of gout, enzyme preparations, diabetic drugs, antioncotics, antihistaminics, drugs for stimulation treatment, antibiotics, chemotherapeutics, biological preparations, anthelmintics, anti-Protozoas, drugs for preparations, X-ray contrast media, and diagnostic agents. The composition can be incorporated further together with one or more ingredients to facilitate the ingestion of the present propolis extract as a medical agent. Examples of the ingredients are adjuvants, diluents, bodies, stabilizers, carriers, colorings, flavorings, antiseptics, and preservatives. The resultant composition can be desirably formed for application. Examples of the forms are extracts, elixirs, capsules, granules, pills, ointments for eye, suspensions, emulsions, plasters, suppositories, powders, alcohol preparations, tablets, syrups, infusions, feeding fluid, decoctions, injections, tinctures, ophthalmic solutions, troches, ointments, cataplasms, aromatic water, liniments, lemonades, fluidextracts, lotions, nasal drops, nasal nebulas, inhalants for lower airway, sustained release drugs for eye, oral mucosal patches, and enemas. A dosage per day of the present propolis extract for pharmaceutical use is selected dependently on the aims and administration routes, usually from 0.01 mg to 100 mg for an adult human. The present biologically active composition, containing the present propolis extract which is a natural product with biological activities, does not induce harmful side effects to mammals and humans even in daily uses. Therefore healthy humans also can use present composition in daily lives, without anxieties, to prevent the susceptive diseases and improve living activities.

The biologically active composition of this invention can be also used as, for example, an antiseptic and antioxidant, because the composition bears the biological activities inherent in propolis. The present composition for such uses can be used in the fields, including those of foods, cosmetics, and pharmaceuticals, that must suppress proliferation of microbes and oxidization of effective ingredients. As an antiseptic and antioxidant, the present propolis extract can be used alone or together with one or more commonly feasible ingredients in respective fields. Examples of the feasible ingredients are antiseptics and antioxidants other than propolis extracts, preservatives, solvents, solubilizers, viscocitizers, and flavorings. Depending on the purposes, the composition is prepared into solution, suspension, syrup, paste, powder, granule and other desired solid forms to meet the particular final uses. The composition can be used as a starting or intermediate material to be added to foods, cosmetics, pharmaceuticals, germicidal agents, and antimicrobial agents; effecting antisepsis, antioxidation, preservation, germicide, antimicrobe, etc., in the final products. The composition can be also used by itself as an antiseptic or antioxidant which is used by spraying or coating to daily utensils. The present composition directed to use as an antiseptic or antioxidant contains the present propolis extract in an amount of 0.01% (w/w) or more, preferably, 0.1% (w/w) or more (d.s.b.).

The present propolis extract can exhibit remarkable antimicrobial activity against fungi, yeasts, bacteria, algae, etc. The extract is therefore useful in a germicidal or antimicrobial agent which is applied not only to humans directly but also to daily articles. For such use, the present propolis extract is usually mixed with a desirable solvent or diluent and additional ingredients selected depending on the uses. Examples of the additional ingredients are metals such as silver, salts such as zeolite (a type of aluminosilicate), flavorings, colorings, propellants, surfactants, binder resins, pH modulators, and buffers. The resultant mixtures can be provided after being impregnated in or applied to a paper, film, sheet, cloth, non-woven fabric, hard foam rubber, semi-soft foam rubber, or soft foam rubber, or packed in tubes, spray cans, or bottles.

The germicidal agent and antimicrobial agent according to this invention can be used similarly as conventional ones, for example, by wholly or partly spraying or coating to articles susceptible to microbial contamination. Examples of the articles to be coated or sprayed are personal articles including clothes, caps, hats, shoes, blades, hair setting or styling utensils, toothbrushes, watches, glasses, bags, purses, umbrellas, and parasols; writing utensils including pens and pencils; household supplies including beds, bed clothes, air conditioners and filters thereof, cleaners, humidifiers, remote controllers, toys, sinks, toilet bowls, doorknobs, toilet papers, bath tubs, curtains, shower curtains, carpets, rugs, children's chairs, partitions for children, and waxes; kitchen utensils including refrigerators, can openers, toasters, cooking utensils, juicers, cooking knives, pans, mixers, weights, sieves, strainers, sponges, and lunch boxes; daily necessaries including soaps, detergents, wet towels, wet tissue papers, towels, and mats; building materials including adhesives, caulking agents, concretes, cements, mastics, and paints; communication media including telephones, calculators, office computers, cameras, video cameras, rental video tapes, rental records, and rental books; games including mahjongg tiles, playing cards, chessboards and chessmen (including Japanese style, i.e., "Shogiban" and "Shogi-no-koma"), and checkerboards and checkermen (including Japanese style, i.e., "Goban" and "Goishi"); athletic utensils or instruments, musical instruments, sanitary napkins and tampons, credit cards, and handles and steering wheels of cars. The present germicidal agent and antimicrobial agent can be used further together with other antiseptics and, if possible, incorporated in the articles as mentioned above during their production processes by the step of mixing, kneading, dissolving, injecting, or soaking.

The addition of organic acids to the present propolis extract can enhance one or more of the biological activities thereof. The wording "organic acid" as referred to in this invention includes any organic acid, including its derivatives such as salts, that can be incorporated in foods, cosmetics, pharmaceuticals, germicidal agents, or antimicrobial agents. Examples of the organic acids are citric acid, lactic acid, DL-tartaric acid, L-tartaric acid, acetic acid, butyric acid, dehydrobutyric acid, adipic acid, propionic acid, fumaric acid, malic acid, L-aspartic acid, L-glutamic acid, cinnamic acid, L-ascorbic acid, nicotinic acid, folic acid, gluconic acid, benzoic acid, sorbic acid, boric acid, trisodium citrate, monopotassium citrate, sodium lactate, calcium lactate, sodium DL-tartrate, potassium L-tartrate, sodium L-tartrate, sodium acetate, calcium propionate, sodium propionate, monosodium fumarate, sodium L-aspartate, calcium L-glutamate, sodium dehydroacetate, sodium benzoate, and potassium sorbate. These examples can be used in combination, if necessary. To the present propolis extract, the organic acids in a solid form can be added at a ratio of 1/2-fold or more, preferably one to 40 times, on a dry solid basis; and in a liquid form, 1/2-fold or more, preferably one to 40 times, by liquid weight to the total dry solid weight of the extract. The most preferable organic acid is citric acid. For example, the present propolis extract mixed with five times its weight of citric acid exhibits antimicrobial activity with a synergistically enhanced intensity, apparently higher than the intensity estimated from the sum of the respective activities. The biologically active composition of this invention which further contains the organic acids is feasible in any field as mentioned above.

The present biologically active composition can be prepared in the form of a composition with, as mentioned above, an antiseptic other than propolis extracts. The wording "antiseptic other than propolis extracts" as referred to in this invention includes any cytostatic or cytocidal compounds against a fungus, yeast, bacterium, or alga that can be incorporated in foods, cosmetics, pharmaceuticals, germicidal agents, or antimicrobial agents. Examples of the antiseptics other than propolis extracts are ε-polylysine, butyl parahydroxybenzoate, propyl parahydroxybenzoate, biphenyl hydroxybenzoate, benzoic acid, sodium benzoate, sorbic acid, and potassium sorbate, which may be also classified with the above-mentioned organic acid. These examples can be used in combination, if necessary. More preferably, the antiseptics effective against fungi are used in this invention. To the present propolis extract, the antiseptics in a solid form can be added at a ratio of 1/2-fold or more, preferably one to 20 times, on a dry solid basis; and in a liquid form, 1/2-fold or more, preferably one to 20 times, by liquid weight to the total dry solid weight of the extract. The biologically active composition of this invention which further contains the antiseptics other than propolis extracts is feasible in any field as mentioned above. The antiseptic ε-polylysine is a natural compound which is effective against fungi and acceptable for incorporation in foods. The present biologically active composition containing ε-polylysine is therefore safely and advantageously used in foods.

The following experiments explain the properties and biological activities of the present propolis extract.

Experiment 1
Preparation of Propolis Extract

One kilogram of Brazilian propolis blocks were, after being crushed into powders, soaked in 5 kg of 30% (v/v) aqueous ethanol at 60° C. for two hours, and then cooled to ambient temperature. The solid layer in the resultant soak was collected by filtration through kieselguhr and filter paper, and soaked in 5 kg of 70% (v/v) aqueous ethanol at 60° C. for two hours for extraction. After being cooled to ambient temperature and being allowed to stand at 4° C. overnight, the liquid layer in the resultant extract was collected by filtration similarly as above. The separated solid layer was soaked as above for re-extraction, and newly formed liquid layer in the resultant of re-extraction was collected by filtration similarly as above and pooled with the above-obtained liquid layer.

To a portion of the pooled liquid layer, 10% (w/w) weight (on a wet weight basis) of any one of the ion-exchange resins shown in Table 1 which were pre-equilibrated with 70% (v/v) aqueous ethanol was added, and the liquid layer was moderately stirred at ambient temperature for one hour. The resultant mixture was centrifuged to collect the supernatant, which was then concentrated and dehydrated in vacuo into a solid of a propolis extract. In the case of using an anion-exchange resin, the resin was used in OH form; and a cation-exchange resin, H form. For combined use of anion- and cation-exchange resins, the mixture of the resins was used at a ratio of one to two on a wet weight basis. For control, another portion of the pooled liquid layer was concentrated and dehydrated into a solid without ion-exchange resin treatment. Thus seven kinds of propolis extract samples in solid form, numbered 1–7, were prepared for testing by the following experiments.

TABLE 1

| Treatment | | |
|---|---|---|
| Anion-Exchange Resin | Cation-Exchange Resin | Sample Numbering |
| AMBERLITE IRA411S (strongly basic) | — | 1 |
| DUOLITE A-30B (intermediately basic) | — | 2 |
| DIAION WA-30 (weakly basic) | — | 3 |
| DIAION WA-30 (weakly basic) | SK1B (strongly acidic) | 4 |
| AMBERLITE IRA411S (strongly basic) | SK1B (strongly acidic) | 5 |
| — | SK1B (strongly acidic) | 6 |
| — | — | 7 |

Experiment 2
Sensory Test

The seven samples of Experiment 1 were subjected to a test for the peculiar odor of propolis in usual manner by six panels who had adequate experiences of smelling propolis. The results are summarized in Table 2, on the basis of the panels' judgements, with the following four ranks of sensory evaluation on the peculiar odor of propolis: "+++", intense; "++", relatively intense; "+", relatively moderate; and "±", weak or almost none.

TABLE 2

| Sample No. | Sensory Evaluation | Note |
|---|---|---|
| 1 | + | This Invention |
| 2 | ± | This Invention |
| 3 | ± | This Invention |
| 4 | ± | This Invention |
| 5 | ± | This Invention |
| 6 | ++ | Reference |
| 7 | +++ | Control |

As shown in Table 2, the peculiar odor of propolis was remarkably reduced in the samples 1 to 5 as compared to the sample 7 for control.

Experiment 3
Identification of Odorizing Ingredient

The seven samples of Experiment 1 were analyzed by gas chromatography using p-ethyl phenol as internal standard as follows. A sample was precisely weighed out for 250 mg and dissolved in 5 ml of methanol. To the solution, 0.25 ml of 10,000 ppm p-ethyl phenol of methanol solution was added, and 2 μl of the resultant mixture was analyzed. The column used was a capillary column chemically bound with polyethyleneglycol nitroterephthalate as liquid phase, "TC-FFAP" (0.53 mm in internal diameter and 30 m in length, commercialized by GL Sciences Inc., Tokyo, Japan); and the chromatograph, "GC-17B" (commercialized by Shimadzu Corp., Kyoto, Japan). Helium gas was used as carrier gas at a flow rate of 10 ml/min. The temperature of sample injection gate was set at 250° C. The temperature in the column was programmed to remain at 40° C. for five minutes after sample injection, rise at a rate of 5° C./min, and then remain at 230° C. The detection was with a hydrogen flame ionization detector. FIGS. 1 and 2 show, as typical results, the gas chromatograms of the samples 3 and 7, respectively.

The ingredients separated by gas chromatography as mentioned above were next by a sensory test on odor according to "GC Sniff method", described in Koji Wada et al., "Agricultural and Biological Chemistry", Vol.51, No.7, pp.1753–1760 (1987). In this test, gas released from the detector was directly smelled after hydrogen flow to the detector was suspended and the flame stifled. Then, the above-obtained gas chromatograms were studied by referring to the results of this sensory test, resulting in the identification of two major odorizing or odoriferous ingredients: on gas chromatography using p-ethyl phenol as internal standard, one gives a relative retention time of 0.7–0.8 against p-ethyl phenol; and the other, a relative retention time of 1.2–1.3 against p-ethyl phenol. The ingredients were designated "A" and "B", respectively. On the basis of the peak areas in the chromatograms, the contents of the ingredients A and B were calculated for the samples 1–7. The results are in Table 3.

TABLE 3

| Sample No. | Contents (mg/g) | | Note |
|---|---|---|---|
| | Ingredient A | Ingredient B | |
| 1 | 2.35 | 33.2 | This Invention |
| 2 | 2.07 | 27.7 | This Invention |
| 3 | 1.66 | 36.2 | This Invention |
| 4 | 1.80 | 24.5 | This Invention |
| 5 | 2.09 | 16.9 | This Invention |
| 6 | 3.37 | 27.9 | Reference |
| 7 | 4.49 | 66.5 | Control |

As shown in Table 3, the sample 7 for control, which intensely exhibited the peculiar odor of propolis, contained 4.49 mg of the ingredient A and 66.5 mg of the ingredient B per gram by dry weight. On the contrary, the samples 1–5 exhibited apparently-reduced peculiar odor and contained less of both ingredients, at the respective amounts less than 2.5 mg and less than 40 mg per gram by dry weight. The strongly basic anion-exchange resin "AMBERLITE IRA411S" (commercialized by Rohm and Haas Co., Philadelphia, Pa., U.S.A.), employed for the sample 1, was relatively less efficient in reducing the odorizing ingredients, particularly in reducing the ingredient A, but the resin efficiently decreased both ingredients when used in combination with the strongly acidic cation exchange resin as shown by the results of the sample 5. The results of the sample 6 indicate that the cation exchange resin is less efficient in reducing the odorizing ingredients when used alone.

Experiment 4

Antimicrobial Activity

The samples 1–7 of Experiment 1 were tested for minimal inhibitory concentrations (MICs) against the proliferation of microbes in accordance with the method described in Japanese Society of Chemotherapy, "Chemotherapy", Vol.29, pp.76–79 (1987) and Vol.27, pp.559–560 (1979). For the test media, sensitivity disc agar plates were prepared to contain any one of the samples 1–7 at concentrations of 500 µg/ml and its serial 1/2 dilutions. The microbes in Table 4 were, after being proliferated in the usual manner, streaked were on the media with a platinum loop and cultured at 27° C. for 24 hours. Thereafter the media were macroscopically examined for colony formation in comparison with control media free of the samples to determine MICs. The results are in Table 4.

TABLE 4

| Microbe (strain') | MIC (µg/ml) | | | | | | |
|---|---|---|---|---|---|---|---|
| | 1" | 2" | 3" | 4" | 5" | 6" | 7" |
| *Microsporum gypseum* (IFO 8231) | 31.3 | 31.3 | 31.3 | 62.5 | 62.5 | 31.3 | 31.3 |
| *Bacillus cereus* (IFO 466) | 62.5 | 62.5 | 62.5 | 125 | 125 | 62.5 | 62.5 |
| *Pseudomonas aeruginosa* (IFO 3453) | 125 | 125 | 125 | 250 | 250 | 125 | 125 |
| *Propionibacterium acnes* (JCM 6425$^T$) | 250 | 250 | 250 | 500 | 500 | 250 | 250 |
| *Corynebacterium equi* (IFO 3730) | 62.5 | 62.5 | 62.5 | 125 | 125 | 62.5 | 62.5 |

': The strain of which depository number includes "IFO" is deposited in The Institute for Fermentation, Osaka (Osaka city, Osaka, Japan); and "JCM", in Japan Collection of Microorganisms (in The Institute of Physical and Chemical Research, Wako city, Saitama, Japan).
": The numbers 1–7 are the sample numbers.

As shown in Table 4, the propolis extracts according to this invention (the samples 1–5) exhibited antimicrobial activity with nearly equivalent efficiency to control (the sample 7) and reference (the sample 6). The microbes *Microsporum gypseum, Bacillus cereus, Pseudomonas aerginosa, Propionibacterium acnes,* and *Corynebacterium equi,* employed in this experiment, would be responsible for dermatophytosis, sitotoxism, dermatitis, or diphtheria. The above results, showing wide antimicrobial spectra of the present propolis extract, indicate the effectiveness of the present propolis extract in wide uses including foods, cosmetics, pharmaceuticals, germicidal agents, and antimicrobial agents.

Experiment 5

Toxicity Test

Any one of the samples 1–7 of Experiment 1 was administered to seven-week-old dd mice through peroral routes. No deaths were observed even at the highest dose of 2.5 g/kg of body weight. These results indicate the safety of the propolis extracts of this invention for intake by mammals including humans.

The followings explain the preferred examples of this invention.

EXAMPLE 1

Propolis Extract

One kilogram of Brazilian propolis blocks were, after being crushed into powders, soaked in 5 kg of 30% (v/v) aqueous ethanol at 60° C. for two hours, and then cooled to ambient temperature. The solid layer in the resultant soak was collected by filtration through kieselguhr and filter paper, and soaked in 5 kg of 70% (v/v) aqueous ethanol at 60° C. for two hours for extraction. After being cooled to ambient temperature and allowed to stand at 4° C. overnight, the liquid layer in the resultant extract was collected by filtration similarly as above. The separated solid layer was soaked as above for re-extraction, and the newly formed liquid layer in the resultant re-extraction was collected by filtration similarly as above and pooled with the above-obtained liquid layer. The pooled liquid layer contained about 35% (w/w) dry solids of the material propolis material.

To the pooled liquid layer, 10% weight (on a wet weight basis) of the weakly basic anion-exchange resin "DIAION WA-30" (in OH form, commercialized by Mitsubishi Chemical Corp., Tokyo, Japan) which had been equilibrated with 70% (v/v) aqueous ethanol were added, and the liquid layer was moderately stirred at ambient temperature for one hour. After being separated from the resin by filtration, the liquid layer was concentrated and dehydrated in vacuo into a solid of the propolis extract of this invention. This step with the ion-exchange resin recovered about 75% (w/w) dry solids. By gas chromatography according to Experiment 1, the propolis extract was determined to contain about 1.5 mg of the ingredient A and about 35 mg of the ingredient B per gram by dry weight. In the extract the peculiar odor of propolis is apparently reduced, while the extract retains the biological activities inherent in propolis including antimicrobial activity, antiviral activity, antitumor activity, anti-inflammatory activity, anti-hyperlipemic activity, anti-oxidant activity, ultraviolet ray-absorbing activity, preservative activity, and vitamin P-supplying activity. The extract is useful, by itself and in combination with other ingredients, in the fields of foods, cosmetics, and pharmaceuticals and other fields where the biological activities of propolis are needed.

EXAMPLE 2

Propolis Extract

Liquid layer in resultant extract of propolis was prepared and pooled in accordance with Example 1. To one weight part of the pooled liquid layer, on a wet weight basis, 0.066 weight part of the strongly basic anion-exchange resin "A26" (in OH form, commercialized by Japan Organo Co., Ltd., Tokyo, Japan) and 0.033 weight part of the strongly acidic cation-exchange resin "15WET" (in H form, commercialized by Japan Organo Co., Ltd., Tokyo, Japan) both of which had been equilibrated with 70% (v/v) aqueous ethanol were added, and the liquid layer was moderately stirred at ambient temperature for one hour. The liquid layer was then, in accordance with Example 1, separated from the resins, concentrated, and dehydrated in vacuo into a solid of the propolis extract of this invention. This step with the ion-exchange resins recovered about 70% (w/w) dry solids. By gas chromatography according to Experiment 3, the propolis extract was determined to contain about 1.8 mg of the ingredient A and about 20 mg of ingredient B per gram by dry weight. In the extract the peculiar odor of propolis is apparently reduced, while the extract retains the biological activities inherent in propolis including antimicrobial activity, antiviral activity, antitumor activity, anti-inflammatory activity, anti-hyperlipemic activity, anti-oxidant activity, ultraviolet ray-absorbing activity, preservative activity, and vitamin P-supplying activity. The extract is useful, by itself and in combination with other ingredients, in the fields of foods, cosmetics, and pharmaceuticals and other fields where the biological activities of propolis are needed.

EXAMPLE 3

Propolis Extract

The weakly basic anion-exchange resin "DIAION WA-30" (in OH form, commercialized by Mitsubishi Chemical Corp., Tokyo, Japan) and the strongly acidic cation-exchange resin "SK1B" (in H form, commercialized by Mitsubishi Chemical Corp., Tokyo, Japan) were packed in a stainless steel column in a ratio of two to one by wet weight. After equilibration of the column with 70% (v/v) aqueous ethanol, to the column a liquid layer prepared and pooled by the method in Example 1 was applied, and 70% (v/v) aqueous ethanol was run at a flow speed of SV3. The eluate from the column was collected, evaporated, and dehydrated in vacuo into a solid of the propolis extract of this invention. This step recovered about 75% (w/w) dry solids. By gas chromatography according to Experiment 3, the propolis extract was determined to contain about 1.8 mg of the ingredient A and about 25 mg of the ingredient B per gram by dry weight. In the extract the peculiar odor of propolis is apparently reduced, while the extract retains the inherent activities, including antimicrobial activity, antiviral activity, antineoplastic activity, anti-inflammatory activity, anti-hyperlipemic activity, anti-oxidant activity, ultraviolet absorbing activity, preserving activity, and vitamin P-supplying activity. The extract is useful, by itself and in combination with other ingredients, in the fields of foods, cosmetics, and pharmaceuticals and in other fields where the biological activities of propolis are needed.

EXAMPLE 4

Biologically Active Composition

A type of the biologically active composition of this invention was prepared by dissolving one weight part of the propolis extract of Example 1, four weight parts of citric acid, and three weight parts of $\epsilon$-polylysine in 32 weight parts of 70% (v/v) aqueous ethanol. The composition exhibits the biological activities inherent in propolis, particularly remarkable in anti-microbial activity, while the peculiar odor of propolis therein is reduced. The product is useful as a material for foods, cosmetics, and pharmaceuticals to maintain or promote health, and as an antiseptic, preservative, fungicide, and antioxidant feasible in the products.

EXAMPLE 5

Biologically Active Composition

A type of the biologically active composition of this invention was prepared by dissolving one weight part of the propolis extract of Example 2 and five weight parts of acetic acid in 54 weight parts of 70% (v/v) aqueous ethanol. The composition exhibits the biological activities inherent in propolis, particularly remarkable in antimicrobial activity, while the peculiar odor of propolis therein is reduced. The composition is useful as a material for foods, cosmetics, and pharmaceuticals to maintain or promote health, and as an antiseptic, preservative, fungicide, and antioxidant feasible in the products.

EXAMPLE 6

Biologically Active Composition

The propolis extract of Example 3 was crushed in the usual manner into powders, and a type of the biologically active composition of this invention was prepared by mixing one weight part of the powders with two weight parts of citric acid into homogeneity. The composition exhibits the biological activities inherent in propolis, particularly remarkable in antimicrobial activity, while the peculiar odor of propolis therein is reduced. The composition is useful as a material for foods, cosmetics, and pharmaceuticals to maintain or promote health, and as an antiseptic, preservative, fungicide, and antioxidant feasible in the products.

EXAMPLE 7

Gummy Candy

One hundred and fifty weight parts of a hydrogenated maltooligosyl saccharide syrup, "MABIT®" (commercialized by Hayashibara Shoji, Inc., Okayama, Japan), were concentrated by evaporation with heating to a relative moisture of about 15% (w/w). To the concentrate the following materials were added: 13 weight parts of gelatine which had been dissolved in 18 weight parts of water, one weight part of the propolis extract of Example 1, two weight parts of citric acid, and appropriate amounts of a coloring and flavoring. The resultant mixture was formed into gummy candies and then packed.

The product, which hardly causes carious teeth and exhibits a good texture and flavor, is useful as a health food to maintain or promote health.

EXAMPLE 8

Chewing Gum

To three weight parts of a gum base which had been heated to melt into softness, the following materials were added: four weight parts of sucrose, three weight parts of maltose powders, 0.02 weight part of the propolis extract of Example 2, and an appropriate amount of a coloring. The resultant mixture was kneaded and formed with a roller into chewing gum, which was then packed.

The product, which hardly causes carious teeth and exhibits a good texture and flavor, is useful as a health food to maintain or promote health.

EXAMPLE 9

Snack

Potatoes were stored to autodigest reducing sugars in the usual manner at a temperature of 20° C. and a relative humidity of 85% for two weeks, then washed with water, peeled, selected, and sliced 1.5 mm thick with a centrifugal slicer. The slices were washed with water to remove the surface starch, drained, fried with oil at 170° C. for about five minutes, and removed from oil. A seasoning powder was prepared by mixing six weight parts of salt, three weight parts of food grade trehalose powders "TREHAOSE®" (commercialized by Hayashibara Shoji, Inc., Okayama, Japan), and appropriate amounts of the propolis extract of Example 1 and spices, and the seasoning was added adequately to the slices with a salter. The seasoned slices were transferred to a weighing packer, where the slices were weighed, packed, and sealed. Thus a snack was obtained.

The product, with a good texture and flavor, is useful as a health food to maintain or promote health.

EXAMPLE 10

Tea Bag

Nine weight parts of lyophilized black tea extract powders which had been dissolved in an appropriate amount of water were mixed with one weight part of the propolis extract of Example 2 which had been dissolved in an appropriate amount of ethanol. With the resultant mixture, ninety weight parts of black tea leaves were sprayed, after being fermented and dehydrated in the usual manner. The leaves were sieved out, cut into pieces, dried for completion, separated from impurities with a separator, and divided and packed into two grams per bag of Japanese paper. Thus tea bags were obtained.

For use to drink, a bag of the product is soaked in about 180 ml of cold water for ten minutes or in hot water (90° C. to 100° C.) for two minutes. The product, with good taste and flavor, is useful as a health food to maintain or promote health.

EXAMPLE 11

Custard Cream

The following materials were mixed in the usual the manner: 100 weight parts of corn starch, 40 weight parts of food grade trehalose powders "TREHAOSE®" (commercialized by Hayashibara Shoji, Inc., Okayama, Japan), 60 weight parts of trehalose-containing syrup "TREHASTAR®" (commercialized by Hayashibara Shoji, Inc., Okayama, Japan), 80 weight parts of maltose, 20 weight parts of sucrose, and 0.25 weight parts of the propolis extract of Example 6, before being mixed with 280 weight parts of hen eggs. Into the resultant mixture 1,000 weight parts of milk were moderately poured, and the mixture was stirred over fire till corn starch was gelatinized so as to be wholly translucent. After the fire was stifled, an appropriate amount of a vanilla flavoring was added to the mixture, which was then weighed, divided, and packed. Thus a custard cream was obtained.

The product, with mild luster and improved preservative activity, is useful as a health food to maintain or promote health.

EXAMPLE 12

Supplemental Health Food

The following materials were mixed in the usual manner: 52 weight parts of food grade trehalose powders "TREHAOSE®" (commercialized by Hayashibara Shoji, Inc., Okayama, Japan), 40 weight parts of corn starch, 3.5 weight parts of propolis extract of Example 3, and 2.5 weight parts of cellulose crystals. The resultant mixture was kneaded under an appropriate amount of water spray and granulized in fluid. The granules were pulverized and spherized into material powders for tablets. The powders were admixed with two weight parts of sucrose fatty acid ester as a surfactant into homogeneity and processed by using a tablet machine with a punch (11 mm in diameter) into tablets (about 300 mg/tablet).

The product, which is easily ingestible and decayable in alimentary canals, is also useful as a health food to keep or enhance health.

EXAMPLE 13

Hair Rinse

The following materials were mixed in the usual manner: one weight part of food grade trehalose powders "TREHA-OSE®" (commercialized by Hayashibara Shoji, Inc., Okayama, Japan), two weight parts of the propolis extract of Example 1, two weight parts of α-glucosyl rutin powders "αG Rutin" (commercialized by Toyo Sugar Refining Co., Ltd., Tokyo, Japan), two weight parts of distearyl methylene ammonium chloride, two weight parts of cetanol, two weight parts of silicon oil, one weight part of polyoxyethylene oleyl alcohol ether, and an appropriate amount of a flavoring. The mixture was heated into a solution, to which a mixture of three weight parts of 1,3-butylene glycol, 85 weight parts of refined water, and an appropriate amount of an antiseptic were added under stirring conditions. The resultant mixture was cooled, and thus a hair rinse was obtained.

The product, which is stable and does not irritate scalps, is also useful as a cosmetic to keep or promote healthy conditions of scalps and hair.

EXAMPLE 14

Milky Lotion

The following materials were mixed in the usual manner: 0.5 weight part of polyoxyethylene behenylether, one weight part of polyoxyethylene sorbitol tetraoleate, one weight part of lipophilic glycerol monostearate, 0.5 weight part of pyruvic acid, 0.3 weight part of behenyl alcohol, 0.3 weight part of maltitol, one weight part of avocado oil, one weight part of the propolis extract of Example 3, and appropriate amounts of vitamin E and an antiseptic. The mixture was heated into a solution, to which one weight part of sodium L-lactate, seven weight parts of 1,3-butyleneglycol, 0.1 weight part of carboxyvinyl polymer, and 86.3 weight parts of refined water were added. The resultant mixture was emulsified with a homogenizer and mixed by stirring with an appropriate amount of a coloring. Thus a milky lotion was obtained.

The product, which is less sticky and satisfactorily extendable, is useful as a cosmetic to maintain or promote healthy conditions of skins.

EXAMPLE 15

Bath Liquid

Twenty-one weight parts of sodium DL-lactate, eight weight parts of sodium pyruvate, five weight parts of the propolis extract of Example 2, 40 weight parts of ethanol, 26 weight parts of refined water, and appropriate amounts of a coloring and flavoring were mixed in the usual manner. Thus a bath liquid was obtained.

The product is used for bath in 1/100 to 1/10,000 dilution with warm or cool water. The product, with effectiveness of cleansing and whitening skins and antimicrobial activity, is useful also as a cosmetic to maintain or promote skin health.

EXAMPLE 16

Toothpaste

A toothpaste was prepared by mixing in the usual manner the following materials: 45 weight parts of calcium secondary phosphate, 2.9 weight parts of pullulan, 1.5 weight parts of sodium lauryl sulfate, 20 weight parts of glycerine, 0.5 weight part of polyoxyethylene sorbitan laurate, 10 weight parts of sorbitol, seven weight parts of maltitol, 13 weight parts of refined water, 0.1 weight part of the propolis extract of Example 2, and an appropriate amount of a flavoring.

The product is stable and useful as a toiletry to maintain or promote healthy conditions of mouths.

EXAMPLE 17

Ointment

The following materials were mixed in the usual manner: one weight part of sodium acetate trihydrate, four weight parts of calcium DL-lactate, and 10 weight parts of glycerine. To the resultant mixture, 0.5 weight part of peppermint oil, 49 weight parts of petrolatum, 10 weight parts of Japan wax, 10 weight parts of lanolin, 14.5 weight parts of sesame oil, and one weight part of the propolis extract of Example 3 were added and mixed into homogeneity. Thus an ointment was obtained.

The product, having a satisfactory permeability and extensibility, is useful as a pharmaceutical to maintain or promote health conditions of skins.

EXAMPLE 18

Feeding Fluid

In accordance with the formation in Table 5, the ingredients were mixed (in Table 5, "appropriate" amount corresponds to a half value of the dietary allowance for the life activity level II, moderate, in the report "dietary allowances for Japanese" by Ministry of Health and Welfare of Japan):

TABLE 5

| Ingredient | Blended amount (weight parts) |
| --- | --- |
| powdered skim milk | 43.0 |
| powdered whole milk | 12.0 |
| trehalose *1 | 43.8 |
| the propolis extract of Example 3 | 1.0 |
| vitamin A | appropriate |
| vitamin D | appropriate |
| thiamine hydrochloride | appropriate |
| riboflavine | appropriate |
| pyridoxine hydrochloride | appropriate |
| cyanocobalamine | appropriate |
| choline tartrate | appropriate |
| nicotinamide | appropriate |
| calcium pantothenate | appropriate |
| 2-O-a-D-glucopyranosyl-L-ascorbic acid | appropriate |
| tocopherol acetate | appropriate |
| iron sulfate | appropriate |
| calcium hydrogenphospate | appropriate |
| pullulan *2 | 0.2 |

*1: reagent grade trehalose powders (commercialized by Hayashibara Seibutsu Kagaku Kenkyujo, Inc., Okayama, Japan)
*2: pullulan powders with an averaged molecular weight of 150,000 daltons ("PIF", commercialized by Hayashibara Shoji, Inc., Okayama, Japan)

The resultant mixture was canned under sterile conditions in a content of 500 g/can. Thus a product for a feeding fluid was obtained.

For use, a can of the product is dissolved in once or twice equal weights of cool or slightly warm (at 30° C. to 40° C.) water before feeding. In the case of feeding through peroral routs, the solution can be applied by a single or several divisional shots per day; and through transnasal and gastric or interstitial fistula routs, by a continuous or intermittent flow at a flow rate of about 300 ml/hr. The product, which supplies calories, is useful as a pharmaceutical to maintain or promote health.

EXAMPLE 19

Wet Tissue Paper

A mixture was prepared with 0.5 weight part of the propolis extract of Example 3, one weight part of succinic acid, 0.5 weight part of glycerine, and 98 weight parts of refined water. With the mixture, 40 weight parts of non-woven fabric of cuproxam cellulose fibers were wetted. Thus a wet tissue paper was obtained.

The product, which possesses germicidal and antimicrobial activity but is less irritating to skins, is useful as a daily life utensil to maintain or promote health.

EXAMPLE 20

Antimicrobial Spray

A material liquid was prepared with 68 weight parts of isopropanol, 26 weight parts of refined water, two weight parts of the propolis extract of Example 2, and four weight parts of benzoic acid, which were homogenized in the usual manner. The material liquid was charged together with liquefied carbonic acid gas as a propellant in 100 ml-spray cans at a ratio of 40ml to 60 ml per can. Thus cans with an antimicrobial spray were obtained.

The product, which is safe and with a good germicidal and antimicrobial activity, is useful as a daily life utensil to maintain or promote health.

As described above, this invention was made based on the identification of the odorizing ingredients of propolis and the establishment of the method to decrease the ingredients from propolis extracts without attenuating the inherent biological activities. The peculiar odor of the propolis extract of this invention is apparently lower than that of conventional propolis extracts. The present propolis extract gains a variety of uses in the fields that has rejected use of propolis because of its peculiar odor, such as the fields of foods, cosmetics, pharmaceuticals, and others that can use the biological activities of propolis. The present propolis extract can be produced in desired amounts by the process of this invention comprising the steps of extracting with a hydrophilic organic solvent and treating with an anion-exchange resin.

This invention exhibits these remarkable effects and greatly contributes to the art.

While there has been described what is at present considered to be the preferred embodiments of this invention, it will be understood the various modifications may be made therein, and it is intended to cover in the appended claims all such modifications as fall within the true spirits of the invention.

We claim:

1. A method for producing a propolis extract having a reduced content of at least one odorizing ingredient selected from odorizing ingredients having a relative retention time against p-ethyl phenol of 0.7 to 0.8 as determined by gas chromatography using p-ethyl phenol as an internal standard and odorizing ingredients having a relative retention time against p-ethyl phenol of 1.2–1.3 as determined by gas chromatography, and mixtures thereof, comprising:

soaking propolis in a hydrophilic organic solvent to effect extraction; and treating the liquid layer in the resultant extract with an anion exchange resin.

2. The process according to claim 1 wherein the hydrophilic organic solvent is selected from the group consisting of methanol, ethanol, n-propanol, and isopropanol, optionally mixed with water.

3. The process according to claim 1 wherein the hydrophilic organic solvent is ethanol.

4. The process according to claim 1 wherein the anion exchange resin is used in combination with a cation exchange resin.

* * * * *